(12) United States Patent
Pagani

(10) Patent No.: US 10,267,849 B2
(45) Date of Patent: Apr. 23, 2019

(54) SENSING STRUCTURE OF ALIGNMENT OF A PROBE FOR TESTING INTEGRATED CIRCUITS

(71) Applicant: STMicroelectronics S.r.l., Agrate Brianza (IT)

(72) Inventor: Alberto Pagani, Nova Milanese (IT)

(73) Assignee: STMicroelectronics S.r.l., Agrate Brianza (IT)

( * ) Notice: Subject to any disclaimer, the term of this patent is extended or adjusted under 35 U.S.C. 154(b) by 0 days.

(21) Appl. No.: 15/848,996

(22) Filed: Dec. 20, 2017

(65) Prior Publication Data

US 2018/0113168 A1    Apr. 26, 2018

Related U.S. Application Data

(63) Continuation of application No. 14/754,906, filed on Jun. 30, 2015, now Pat. No. 9,880,219, which is a
(Continued)

(30) Foreign Application Priority Data

Jun. 10, 2010 (IT) .............................. VI2010A0159

(51) Int. Cl.
| | |
|---|---|
| *B06B 1/00* | (2006.01) |
| *G01R 31/28* | (2006.01) |
| *C12Q 1/00* | (2006.01) |
| *G01R 1/067* | (2006.01) |
| *H01L 21/66* | (2006.01) |

(Continued)

(52) U.S. Cl.
CPC ............ *G01R 31/2891* (2013.01); *C12Q 1/00* (2013.01); *G01R 1/06794* (2013.01); *G01R 31/2884* (2013.01); *H01L 22/34* (2013.01); *B06B 2201/00* (2013.01); *C12Q 2304/00* (2013.01); *C12Q 2326/00* (2013.01); *G01N 1/00* (2013.01); *G01R 11/00* (2013.01); *H01L 21/00* (2013.01);
(Continued)

(58) Field of Classification Search
CPC ....... H01L 21/00; H01L 2221/00; G01N 1/00; B06B 1/00; B06B 2201/00; G01R 11/00
See application file for complete search history.

(56) References Cited

U.S. PATENT DOCUMENTS

| | | | |
|---|---|---|---|
| 5,014,003 A | 5/1991 | Ishikawa | |
| 5,065,092 A | 11/1991 | Sigler | |

(Continued)

OTHER PUBLICATIONS

IT Search Report and Written Opinion for IT VI2010A000159 dated Feb. 9, 2011 (7 pages).

*Primary Examiner* — Jermele M Hollington
*Assistant Examiner* — Temilade S Rhodes-Vivour
(74) *Attorney, Agent, or Firm* — Crowe & Dunlevy

(57) ABSTRACT

A sensing structure is presented for use in testing integrated circuits on a substrate. The sensing structure includes a probe region corresponding to a conductive region for connecting to the integrated circuit. A first sensing region at least partially surrounds the probe region. A plurality of sensing elements connects in series such that a first of the plurality of sensing elements has two terminals respectively connected to the first sensing region and the probe region. And a second of the plurality of sensing elements has two terminals respectively connected to the probe region and a first reference potential.

22 Claims, 14 Drawing Sheets

Related U.S. Application Data continuation of application No. 13/155,623, filed on Jun. 8, 2011, now Pat. No. 9,134,367.

(51) Int. Cl.
  *H01L 21/00* (2006.01)
  *G01N 1/00* (2006.01)
  *G01R 11/00* (2006.01)

(52) U.S. Cl.
  CPC ...... *H01L 2221/00* (2013.01); *H01L 2924/00* (2013.01)

(56) References Cited

U.S. PATENT DOCUMENTS

| | | |
|---|---|---|
| 5,406,209 A | 4/1995 | Johnson et al. |
| 5,744,379 A | 4/1998 | Mandai et al. |
| 5,969,530 A | 10/1999 | Yamashita |
| 6,127,729 A | 10/2000 | Fukuda |
| 7,282,940 B2 | 10/2007 | Hirai |
| 7,612,573 B2 | 11/2009 | Kim et al. |
| 7,616,020 B2 | 11/2009 | Kim et al. |
| 8,067,718 B2 | 11/2011 | Nordstrom et al. |
| 2002/0196031 A1 | 12/2002 | Blades |
| 2003/0184333 A1 | 10/2003 | Nagel et al. |
| 2005/0045879 A1 | 3/2005 | Ausserlechner |
| 2005/0258854 A1* | 11/2005 | Kim ............ G01R 1/06794 324/754.1 |
| 2006/0061368 A1 | 3/2006 | Furse et al. |
| 2006/0161825 A1 | 7/2006 | Lomazzi et al. |
| 2007/0090851 A1* | 4/2007 | Kim ............ G01R 1/06794 324/750.3 |
| 2007/0117253 A1 | 5/2007 | Hsu et al. |
| 2008/0021436 A1 | 1/2008 | Wolpert et al. |
| 2008/0217612 A1* | 9/2008 | Patterson ........... H01L 22/34 257/48 |
| 2009/0160470 A1 | 6/2009 | Reinwald et al. |
| 2009/0273354 A1* | 11/2009 | Dhirani ............ G01N 30/64 324/663 |
| 2010/0213960 A1* | 8/2010 | Mok ............ G01R 31/2889 324/762.03 |
| 2011/0234249 A1 | 9/2011 | Uematsu et al. |
| 2012/0068725 A1* | 3/2012 | Pagani ............ G01R 1/06794 324/750.16 |

* cited by examiner

SENSING STRUCTURE OF ALIGNMENT OF A PROBE FOR TESTING INTEGRATED CIRCUITS

CROSS REFERENCE TO RELATED APPLICATIONS

This application is a continuation of U.S. patent application Ser. No. 14/754,906 filed on Jun. 30, 2015, which is a continuation of U.S. patent application Ser. No. 13/155,623 filed on Jun. 8, 2011 (now U.S. Pat. No. 9,134,367), which claims the priority benefit of Italian patent application number VI2010A000159, filed on Jun. 10, 2010, the disclosures of which are hereby incorporated by reference.

TECHNICAL FIELD

The present invention relates to a structure for use in testing electronic components in a substrate. Moreover, the present invention relates to a substrate including one or more sensing structures and a testing equipment for testing electronic components on a substrate.

BACKGROUND

Thanks to advances in the field of manufacturing processes of electronic integrated circuits, electrical components have become smaller, thereby allowing for manufacturing substrates that include a large number of integrated circuits. Moreover, it is possible to fabricate compact electronic circuits including a large number of components. Consequently, the density of connection terminals for connecting the integrated electronic circuits with other electronic systems has also drastically increased.

After being formed in the substrate, called a wafer, the integrated circuits need to be tested so as to eventually remove faulty components or repair them if this is possible. The functionality of each integrated circuit included in the substrate is verified by means of suitable probes that contact the connection terminals or pad of the integrated circuit to be tested, in technical language called DUT (Device Under Test). More precisely, during the testing process, an automated testing equipment ATE or tester is electrically connected to the wafer on which the electronic components are formed. The interface between the ATE and the wafer is a card of probes, generally called a probe card, including several probes adapted to simultaneously contact the pads of the DUT integrated circuits performing the so-called probing action of the probes on the pads. Said testing procedures of electronic integrated circuits are commonly performed, for example, during electrical test on the wafer, called in technical language Electrical Wafer Sort (EWS), or for a reliability test on wafer, called in the art Wafer Level Burn-in (WLBI).

Since the DUT to be tested includes a very large number of pads close to each other, the probability that the tip of the probe contacts the region surrounding the pad increases. Consequently, the probability of damaging the passivation surrounding the pad, due to improperly performed probing, increases.

In order to avoid damaging the pads and breaking of the passivation, it is therefore crucial to correctly align the tips of the probes of the probe card with corresponding pads in the testing phase of the DUT integrated circuits.

The correct alignment of a probe card with respect to corresponding pads can be electrically performed by using suitable dummy (fictitious) structures formed on the substrate. Examples of such dummy structures or dummy pads are shown in FIGS. 34 and 35. In particular, FIG. 34 illustrates a pad 10 including a first non-conductive region 12, which would be used for the probing in a common conductive pad, surrounded by a conducting region 11 for sensing. A sensing circuit 13 is connected between the conducting sensing region 11 and a ground electrode. The sensing circuit 13 may be a diode, a resistor or the like. The dimensions of the non-conducting region 12 substantially correspond to the dimensions of the connection terminal or pad of the integrated circuit to be tested. In order to verify alignment, the probe tip contacts the dummy pads and a current is forced/absorbed by means of the tip. If the tip contacts the first non-conductive region 12, no current will flow through the pad, and the circuit will be open. On the contrary, if the probe tip contacts the conducting sensing region 11, a current will flow through the pad and a suitable voltage will be detected across the sensing circuit 13, thereby indicating that the probes of the probe card are not correctly aligned with the pads. Several configurations of the dummy pad of FIG. 34 are described in U.S. Pat. No. 7,616,020 (incorporated by reference).

FIG. 35 illustrates a further realization of a dummy pad 20 according to the prior art. The dummy pad 20 includes a probe region 22 for contacting the tip of the probe surrounded by a plurality of conductive sensing regions 21 electrically isolated from each other. Each conductive sensing region 21 is connected to a ground electrode through a sensing circuit 23, 24, 25, 26. Sensing circuits 23, 24, 25, 26 connected to different conducting sensing regions 21 may be diodes of a different area so as to have a different resistance or may be formed by a different number of identical diodes connected in parallel to the sensing region and a ground electrode or ground terminal. As previously described, a current is forced from the probe in order to determine the position of the probe, which, if connected to a conducting sensing region 21, will be connected to a particular sensing circuit 23, 24, 25, 26 in turn connected to a corresponding conducting sensing region 21. Since sensing circuits connected to different conducting sensing regions have different resistances, it is possible to determine which conducting sensing region is being connected to the probe, thereby indicating the drift direction of the probe. The sensing circuits may include diodes of different areas as well as resistors or transistors. Several configurations of the dummy pad depicted in FIG. 35 are described U.S. Pat. No. 7,612,573 (incorporated by reference).

However, the dummy pad 10 illustrated in FIG. 34 only allows detecting whether the probe contacts the sensing structures within or outside the probe region but does not allow determining the drift direction of the probe.

Further, although the dummy pad 20 of FIG. 35 allows determining the drift direction of a probe, the position of the probe is determined by using either a different diode for each sensing region or a different number of identical diodes connected in parallel. Accordingly, the voltage difference measurable between the sensing regions is rather small. More precisely, if the sensing circuits are formed by diodes, said voltage difference lies between 50 mV and 100 mV, which is much less than the threshold voltage of the diode forming the sensing circuit.

However, in the testing process, it often occurs that the probe tip does not contact the corresponding connection terminal perfectly, due, for instance, to oxidation of the tip itself or to imperfections of the pad. This increases the contact resistance between the probe and the connection terminal, thereby causing a variation in the value of measured electrical parameter. This behavior is illustrated in the histograms of FIGS. 36 and 37. In particular, FIG. 36—shows voltage values measured in a case where the probe tip perfectly contacts a pad with a characteristic identical to those of a generic sensing region. On the other hand, if the measuring conditions are not optimal, a significant percentage of measurements will provide a voltage value which can vary by 300 mV and even more from the value measured in optimal/ideal conditions.

Consequently, the structures described in the cited prior art documents are either not capable of determining the drift direction of the probe or will fail to correctly determine the position of the probe in a significant number of measurements.

Moreover, since sensing circuits of different sensing regions are connected in parallel, if the probe tip contacts two neighboring sensing regions, the current will flow through both sensing circuits and the voltage drop that will be measured across both sensing circuits will make it impossible to even approximately determine which sensing region the probe is contacting.

Finally, sensing circuits including integrated resistors may not be accurate since the value of a resistor generally varies, in absolute terms, even more than 25% from the desired value, due for instance to the unevenness of the process parameters in a manner which is known to the skilled persons. In addition, integrated resistors may be quite bulky thereby causing the sensing circuits to occupy a large area in the substrate and increasing costs.

Given these problems with the existing technology, it would be advantageous to provide a sensing structure that has reduced dimensions and is capable of determining the position of a probe in a reliable manner without being affected by poor electrical contact between the probe and the sensing structure.

SUMMARY

Embodiments provide a sensing structure, wherein the difference between voltage values of different sensing regions is larger than the variation in the measured value due to imperfections of the testing system. This enables unambiguous determination of the position of a probe with respect to the sensing structure even in the case that the measurement is not performed in optimal conditions.

In accordance with an embodiment, a sensing structure for use in testing integrated electronic components on a substrate is provided. The sensing structure comprises at least two sensing regions connectable to a probe and at least one first sensing element. Each of the at least one sensing element is connected, for example directly connected, to two sensing regions such that for each sensing region a different value of an electrical parameter is measurable between said sensing region and a first reference voltage so as to determine a drift direction of the probe.

The sensing structure may be advantageously arranged so that the at least one sensing element is further connected to at least one adjacent first sensing element. Advantageously, the first sensing elements may be connected in series.

In this manner, the sensing regions included in the structure are connected to a reference potential through one of more sensing elements, wherein the sensing elements are shared among the sensing regions. This allows for cumulating the effect of the sensing elements so as to create between the sensing regions a voltage or potential difference that allows unambiguous determination of the position of a probe, while using a reduced number of sensing elements arranged in a compact design.

Advantageously, the sensing regions may be arranged such that the difference in the value of the measured electrical parameter of two adjacent sensing regions is increased for each pair of adjacent sensing regions. In this manner an average difference in the value of the electrical parameter of two adjacent sensing regions may be increased. Accordingly, using a limited number of sensing elements it is possible to generate large potential differences between adjacent sensing regions so as to reliably determine the position of a probe.

The sensing structure may advantageously be connected to a second reference potential. Accordingly, one of the first and second reference potentials may be selectively connected to the power supply voltage, while the remaining reference potential may be connected to a ground potential. The sensing structure according to this configuration may therefore be used actively during normal operation of the integrated circuit.

According to an embodiment, the sensing regions may at least partially surround a probe region chosen so as to correspond to a conductive region adapted to be connected to an integrated circuit. Since the probe region may also be the conducting region or pad of an integrated circuit, if a probe is detected as lying outside the probe region it is possible to conclude that the probes used for testing the integrated circuits in the wafer are not correctly centered, thereby allowing for correcting the position of the probe.

Advantageously, the probe region may coincide with one of the sensing regions. In this manner if the probe is within the probe region it is possible to measure a potential, thereby allowing to reliably distinguish whether the probe is within the probe region or in a non-conductive region surrounding the sensing structure.

Alternatively, the probe region may be an electrically conductive material connected to a ground electrode by means of a protection element. In this embodiment, the sensing structure can be used, in contrast to a dummy structure, as an active structure for connecting the integrated circuit to other systems external to the integrated circuit.

Advantageously, the sensing elements may be adapted to conduct a current in a unidirectional manner. In particular, any of the first and second sensing elements and the protection element may include at least a set or a subset of elements chosen among diodes and transistors, suitably connected. Alternatively, resistors, inductors, capacitors, or transmission lines may be used instead as elements adapted to conduct a current in a unidirectional manner.

In an advantageous embodiment, the first sensing element and the protection element have opposing polarizations.

According to a second aspect, an embodiment provides a sensing arrangement including a plurality of sensing structures, wherein at least one sensing region of a first sensing structure is connected to a sensing region of a second sensing structure. Accordingly, it is possible to form clusters of sensing regions connectable to an array of probes all connected to the same sensing elements. This configuration allows reducing the space of a substrate exclusively dedicated to the sensing structure.

The sensing arrangement may also include a plurality of sensing structures wherein the sensing structures are arranged in one or more rows, each row having at least one common sensing region. Moreover, sensing regions of different row may be connected by means of a sensing element.

According to a further aspect, an embodiment relates to a substrate for integrated circuits comprising one or more sensing structures. By means of said sensing structures it is possible to determine whether a matrix, or set or array of probes including a plurality of probes for testing integrated circuits is aligned with respect to the substrate such that each probe is connectable with the corresponding terminal or pad of the integrated circuit.

Advantageously, the substrate may include a passivation surrounding the probe region of each sensing structure and the sensing regions may be formed over the passivation.

The plurality of sensing structures may be arranged on the substrate so as to be connected with respective probes located at the extremities of a probing head. Since the behavior of probes along the edges of a matrix of probes are more largely affected by misalignment, the above described arrangement allows determining with higher precision a misalignment of the probes in the probe card with the corresponding pads.

Moreover, in a further arrangement the sensing structures may be arranged on the substrate based on the moving direction of the probe. Aligning the sensing structure according to the moving direction of a probe allows for reducing the number of sensing regions needed to unambiguously determine the position of the probe.

Embodiments also relate to testing equipment for testing electronic components in a substrate. The testing equipment includes a probe head comprising one or more probes connectable to respective sensing structures.

In a further embodiment, a sensing structure for use in testing an integrated circuit on a substrate, comprises: a layer of non-conductive material having a top surface; a conductive probe region surrounded by the layer of non-conductive material and having a top surface that is co-planar with the top surface of the layer of non-conductive material; a first conductive sensing element region surrounded by the layer of non-conductive material and having a top surface that is co-planar with the top surface of the layer of non-conductive material; wherein the first conductive sensing element region is electrically insulated from the conductive probe region by the layer of non-conductive material; and a layer of passivation material in contact with the top surface of the layer of non-conductive material and having a single opening extending therethrough which exposes the top surfaces of the conductive probe region and the first conductive sensing element region.

BRIEF DESCRIPTION OF THE DRAWINGS

The accompanying drawings are incorporated into the specification and form part thereof to illustrate several embodiments. These drawings together with the description serve to explain the principle of the invention. The drawings are only for the purpose of illustrating preferred and alternative examples of how the invention can be made and used, and are not to be construed as limiting the invention to only the illustrated and described embodiments. Further features and advantages will become apparent from the following and more particular description of the various embodiments of the invention, as illustrated in the accompanying drawings, in which like reference numbers refer to like elements, wherein.

DETAILED DESCRIPTION

In the following description, for explanatory purposes, specific details are set forth in order to provide a thorough understanding of the ideas of the present invention. However, it may be evident that the present invention can be practiced without using these specific details. Furthermore, well know structures and devices are only described in general form in order to facilitate the description thereof.

One problem is based on the observation that with the progress in photo-lithographic technologies, substrates for integrated circuits, such as wafers including integrated circuits, include an increasingly large number of connecting pads closely arranged next to each other. Correctly aligning a probe with the corresponding connection terminal on the substrate during the testing phase has therefore become crucial in order not to damage the area surrounding the connection terminal itself. Said connection terminal may be, for instance, a pad or a bump (protruding contact bump).

Correct alignment of a probe and its corresponding pad can be performed manually by directly checking a mark of the probe (probe mark) left by the tip of the probe on the pad after having performed the testing procedure. However, the increasing need for integrated circuits capable of working at high temperatures requires using very robust materials for the pads and electric connections. Consequently, the probe mark is not always visible on hard materials, thereby making it impossible to visually verify the correct alignment of the probe with the corresponding pad. Therefore, it has become necessary to electronically verify alignment by connecting the tip to specially designed structures and analyzing the value of an electrical parameter for example after forcing an excitation such as a current onto the structure. Said excitation may preferably be continuous but it could alternatively be also variable. However, this kind of measurement sensibly varies depending on the quality of the connection between the probe and the corresponding pad. For example, between the tip of a probe and the corresponding pad often lie oxides and contaminants, which reduce the electrical contact surface between the probe and the pad itself, thereby deteriorating the electrical performance of the contact. This can increase the resistance between the probe and the corresponding sensing structure and thus produce sensible variations in the measured electrical parameters. As a result the testing procedure may produce incorrect results.

According to at least one embodiment, in order to check the position of the probe, a sensing structure is designed to be insensitive to problems due to poor or non-optimal electrical contacts between the sensing structure and the probe.

Figure 1:
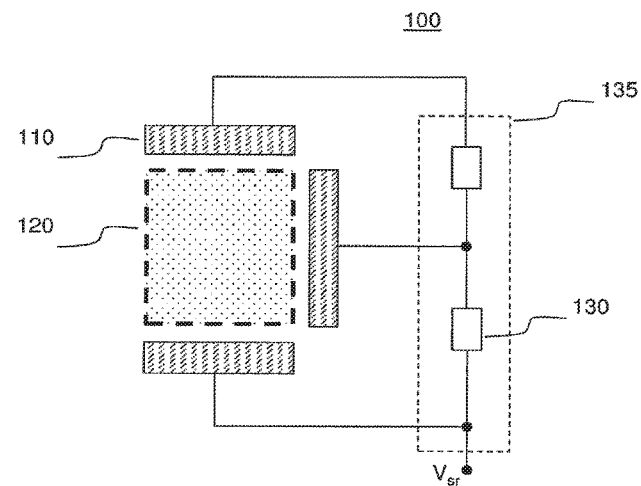
FIG. 1 is a schematic drawing illustrating a sensing structure for use in testing integrated circuits on a substrate.

FIG. 1 illustrates a sensing structure 100 including a plurality of conducting sensing regions 110 or sensing regions. Generally, the sensing regions 110 may be a pad or a bump on the surface of the substrate or wafer. However, any other conducting structure electrically connectable to a conducting element may be used as sensing region 110. The sensing regions 110 are surrounded by an insulating material so as to be electrically isolated. The sensing structure 100 further includes a second region 120, whose dimensions and shape may resemble those of a connection terminal for connecting to a circuit integrated in the substrate. The second region 120 corresponds to a probe region.

In one embodiment, the probe region 120 is non-conductive. However, the probe region 120 can be made of a conducting material. Further, although in this embodiment, the probe region 120 has dimensions substantially equivalent to those of a connecting terminal of an integrated circuit to be tested, in other advantageous embodiments, the probe region 120 may be chosen as being smaller than the area of a generic pad of an integrated circuit, so as to increase the sensibility and reliability of the sensing structure 100.

The sensing regions 110 are connected to a detecting circuit 135 or sensing circuit, which may advantageously comprise a plurality of sensing elements 130 connected to each other in series. Each of the sensing elements 130 is directly connected to two sensing regions 110, such that each pair of sensing regions 110 is connected to at least one sensing element. The sensing structure 100 is connectable to a reference electrode at a predetermined potential $V_{sr}$ so that if a probe induces a current flow onto one of the sensing regions a voltage drop can be measured between the sensing region and the reference potential. Said reference potential will be obtained, for instance, through a connection electrode or terminal (not shown in FIG. 1), which is in turn connected to a probe at the reference potential. A current can be induced in the sensing region by creating, across the sensing region 110 and the reference electrode, an appropriate potential difference.

Figures 2, 3:
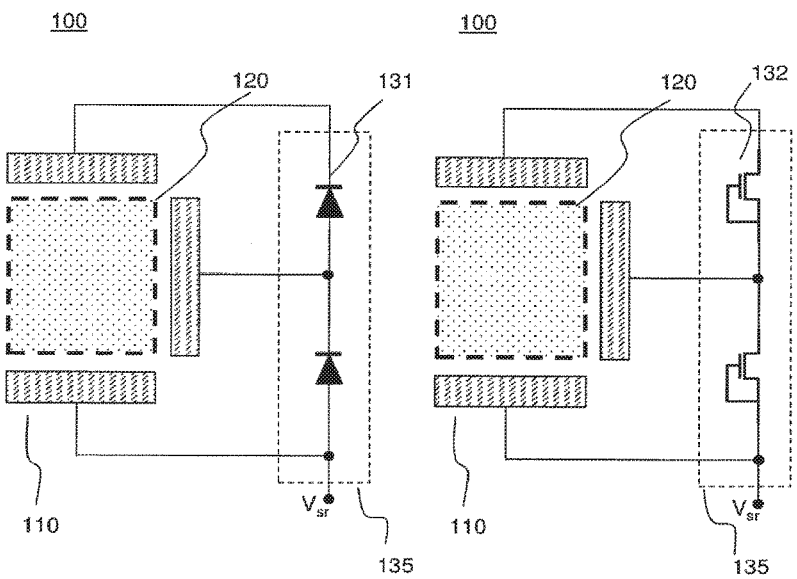
FIGS. 2 to 5 are schematic drawings illustrating alternative realizations of the sensing structure of FIG. 1.

The sensing element 130 is adapted to have a defined voltage drop across its terminals and can include a suitable electronic circuit comprising one or more electrical components. As depicted in FIGS. 2 and 3, the sensing elements may be diodes 131. The sensing diodes 131 may be, for instance, parasitic diodes in the integrated electronic structure included in the substrate and to which said sensing region is connected. In this manner, the dimensions and costs of the sensing structure can be drastically reduced. However, the sensing element 130 may also be a transistor 132, which in FIG. 3 is suitably connected so as to form a transdiode, or a resistor.

Although FIGS. 1 to 3 illustrate an example of sensing structure 100 including three sensing regions 110, the sensing structure 100 may include any number of sensing regions 110. The number of sensing regions 110 may be chosen according to the level of accuracy needed for verifying alignment. Further, although the probe region 120 in FIGS. 1 to 3 is square-shaped, it may be designed to have any shape. As an example, the probe region 120 may be rectangular, hexagonal, octagonal, polygonal, circular, or elliptical. Similarly, also the sensing regions 110 may be designed to have any shape, like for example, one of the shapes listed above. This holds also true for the probing and sensing regions of the other following embodiments.

Figure 4:
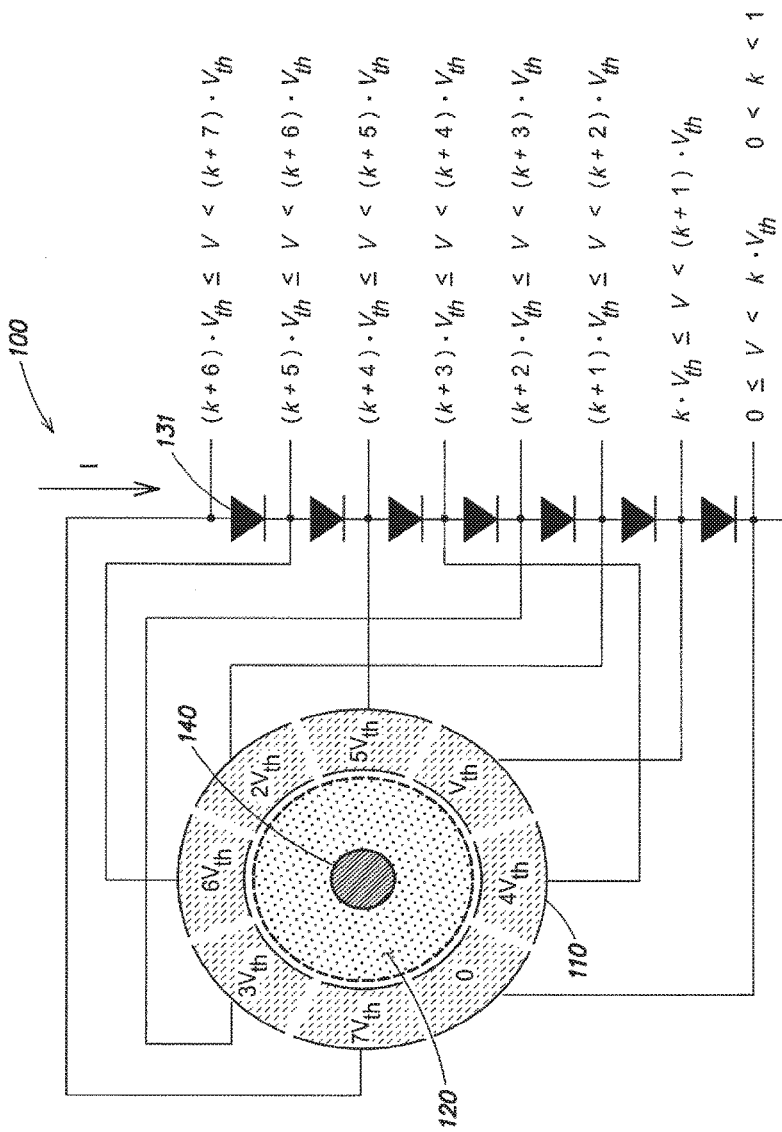

FIG. 4 schematically illustrates the use of a sensing structure 100 including eight sensing regions 110 connected to a series of sensing diodes 131. If a probe 140 is within the insulating probe region 120, there will be no current flowing to the sensing diodes 131, since the probe 140 contacts an insulating material. In this case, the probe can be considered to be correctly aligned.

On the other hand, if the probe 140 contacts one of the sensing regions 110, a current can flow from the probe 140 to the electrode of the reference potential, thereby indicating that the probe 140 is misaligned with respect to the probe region 120. The drift direction of the probe 140 can be determined by measuring the voltage drop across the sensing diodes. In this particular example, the reference potential is a ground potential and the voltage drop between a sensing region and the ground potential is the sum of the voltage drops across the sensing diodes 131 between the sensing region 110 and the ground potential. Since the sensing diodes 131 are connected in series, the voltage measured on adjacent sensing regions will be at least equal or greater (due to the well known non linear characteristic of the diode) to the threshold voltage $V_{th}$ of the particular sensing diode used in the circuit. In the example of FIG. 4, the sensing regions 110 are suitably connected to the sensing diodes 131, so as to create a voltage difference between adjacent sensing regions of at least $3 \cdot V_{th}$.

The probe 140 may be part of a matrix of probes included in a testing system, and said matrix of probes may simultaneously contact a plurality of conducting regions on a substrate. Further, the testing system may be calibrated so as not to be affected by measuring errors due to deteriorated electric contacts or in non-optimal conditions. For example, as shown in FIG. 4, the testing system may be calibrated so as to verify, by means of a suitable electrical test, whether the voltage measured by the probe 140 lies within a predetermined voltage interval defined by a parameter k appropriately chosen based on the particular circuit to be electrically tested and on the used testing system to which the probes belong.

Advantageously, the probe region 120 has a circular shape and as a consequence, the check of the position of the probe 140, performed through the sensing structure 100, does not depend from the moving direction of the probe 140 itself.

Advantageously, knowing the moving direction of the probe 140, it is possible to suitably induce the potentials on the various sensing regions 110 based on the particular needs.

Figure 5:
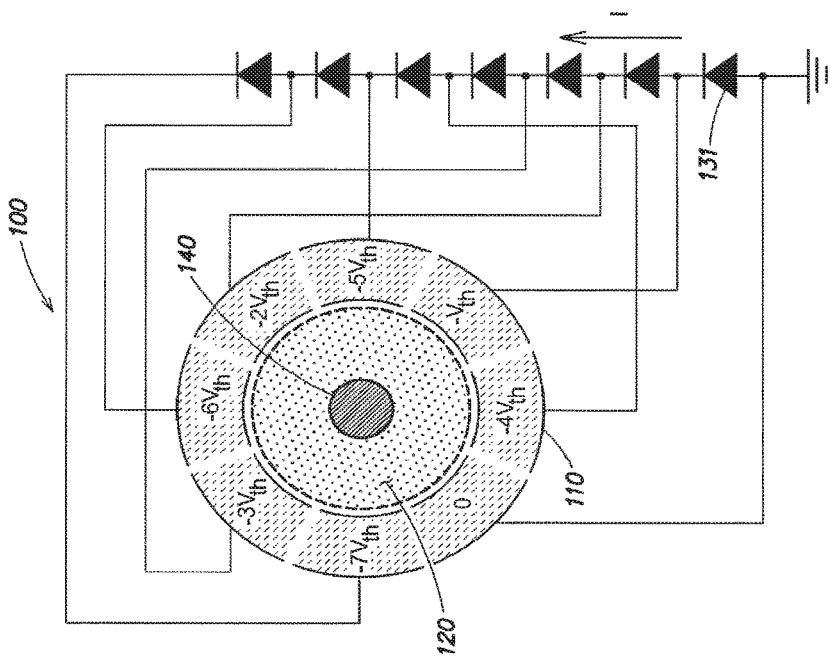

The sensing diodes 131 included in the sensing circuit 135 may also have an opposite polarization with respect to the sensing diodes 131 depicted in FIG. 4. In this case, the current will flow in the opposite direction. This example is shown in FIG. 5. The current induced onto the sensing structure 110 may be thus provided by a special probe connected to a reference terminal in the substrate, which is here connected to ground. Alternatively, the current may be provided/absorbed through a support on which the wafer is arranged.

Figure 6:
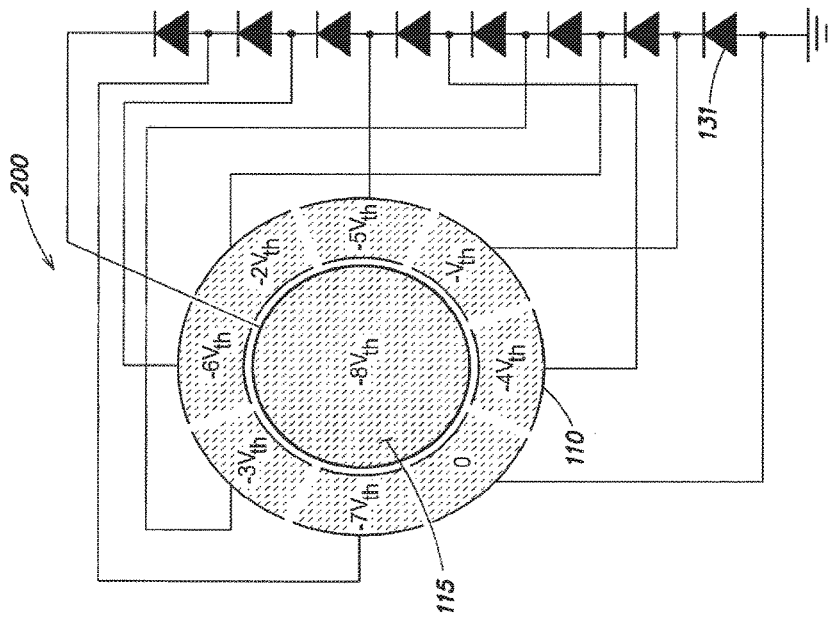
FIG. 6 is a schematic drawing illustrating a sensing structure.

FIG. 6 illustrates a sensing structure 200, including a probe region 115 made of a conducting material and connected to a sensing diode 131 of the sensing circuit 135. If the probe region 115 is connected to the sensing circuit 135, it may be considered to be an additional sensing region. During the test procedure, if the probe 140 is within the probe region 115, an electrical connection will be established between the probe 140 and the probe region 115. Consequently, a current will flow through the sensing circuit 135 and the probe 140 will measure a potential given by the sum of the threshold potentials of sensing diodes 131 connected to the probe region 115 in series. In FIG. 6, eight sensing diodes having the same characteristics are connected in series to the probe region 115 and the ground electrode. Considering the polarization of the diodes 131, the probe will measure a voltage of at least $-8 \cdot V_{th}$ if the probe 140 contacts the sensing structure 200 within the probe region 115.

Figure 7:
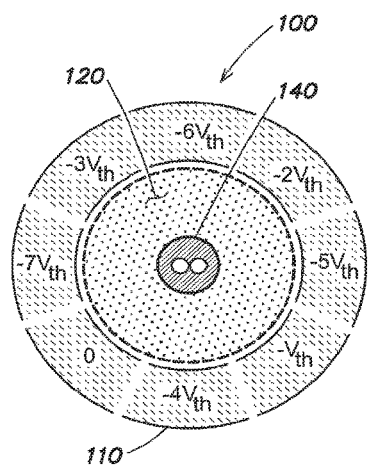
FIGS. 7 to 10 are schematic drawings illustrating a sensing arrangement.
Figure 8:
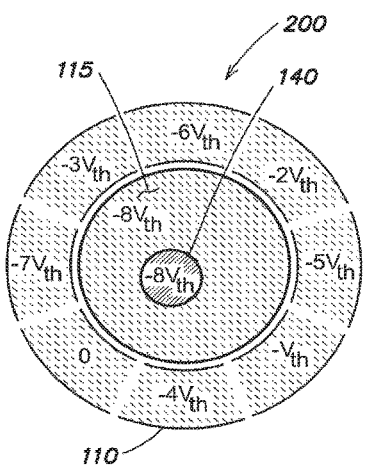

As shown in FIGS. 7 and 8, since probe region 120 of the sensing structure 100 illustrated in FIGS. 1 to 4 is non-conductive, said sensing structure is not capable of determining whether the probe 140 is aligned on the probe region or on any other non-conductive region outside the sensing structure 100. On the contrary, in the sensing structure 200 of FIG. 6, a predefined voltage value can be measured if the probe 140 contacts the sensing structure 200 within the probe region 115. Accordingly, the sensing structure 200 allows determining whether the probe 140 contacts the probe region 115 or any other non-conductive area outside the sensing structure 200.

Figure 9:
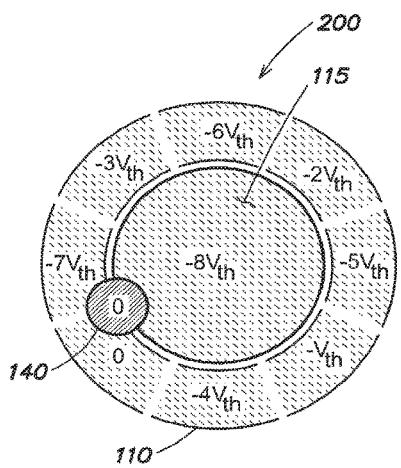
Figure 10:
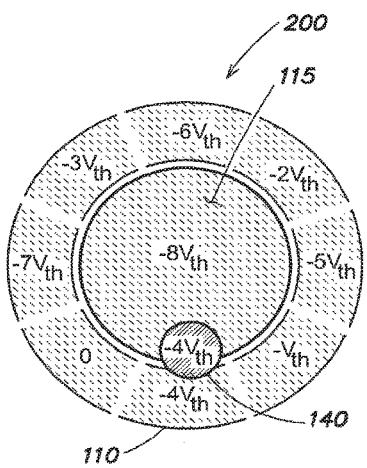

FIGS. 9 and 10 illustrate a situation, wherein more than one sensing region 110 and 115 are simultaneously contacted by the probe 140. Since the sensing regions 110 and 115 are connected to the same circuit of sensing diodes 131 connected in parallel, the current will flow only through the circuit portion that offers less resistance or, in other words, through the path including the smaller number of sensing diodes 131. More precisely, since the sensing regions are short-circuited, the potential drop of the series of diodes between these regions will be zero and these sensing diodes will be non-conducting. Therefore, the current will flow through the remaining diodes connecting the short-circuited sensing regions 110 to the reference potential, and the probe 140 will measure a voltage value given by the sum of the threshold voltages of the diodes crossed by the current. Hence, although two or more sensing regions are short circuited, the probe 140 will assume the potential closest to the ground potential.

More precisely, in FIG. 9 the probe 140 short circuits the sensing region 110 directly connected to a ground electrode and the sensing regions 110 and 115 connected to the ground electrode through 7 and 8 sensing diodes 131, respectively. In this example, all the sensing diodes 131 of the sensing circuit 135 will be at the same potential and the current will flow through the connection line directly connected to the ground electrode. As a consequence, the probe 140 will measure a null voltage.

Similarly, in the example of FIG. 10, the probe 140 short circuits the sensing region 115 connected to the ground through eight sensing diodes 131 and the sensing region 110 connected to the ground through four sensing diodes 131. Again, the sensing diodes 131 connected to the sensing regions 110 and 115 are at the same potential. Therefore, current will flow only through the first four sensing diodes 131 connecting the sensing regions 110 to the ground electrode and the probe 140 will measure a voltage of $-4 \cdot V_{th}$.

The probe region 115 may also be connected to a protection element 133 for protecting circuits from electrostatic discharge and belonging to the ESD (ElectroStatic Discharge) protection circuits. Such protection element may be a diode.

Figure 11:
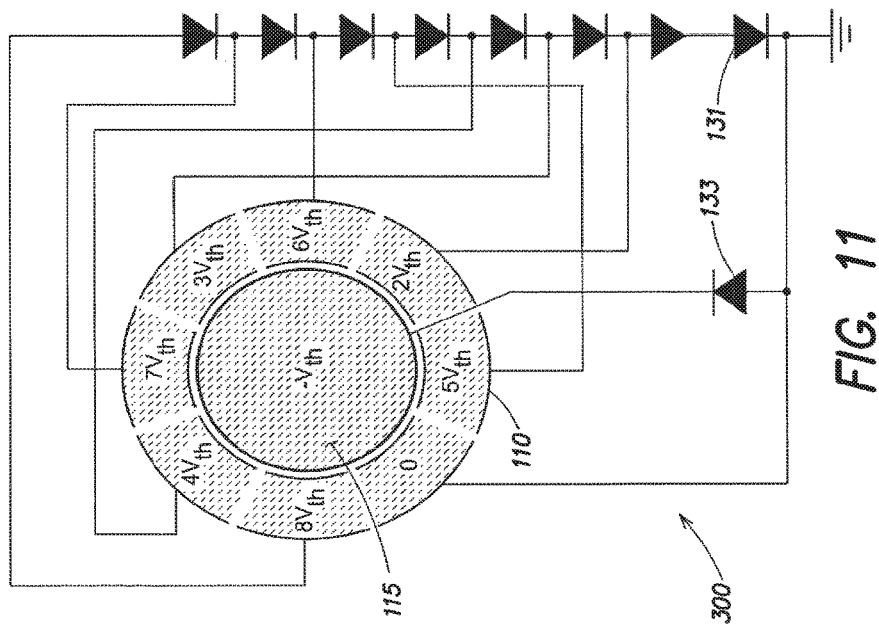
FIG. 11 is a schematic drawing illustrating a sensing arrangement.

FIG. 11 shows a sensing structure 300 where the probe region 115 is connected to the ground electrode through a protection diode 133, while the sensing regions 110 are connected to the sensing circuit 130. The protection diode 133 and the sensing diodes 131 have opposing polarizations. If the probe 140 contacts the probe region 115, a current will flow through the protection diode 133 and the probe region 115 will assume a potential of $-V_{th}$. On the contrary, if the probe 140 contacts one of the sensing regions 110, a current will flow through the sensing diodes 131 and the probe 140 will measure a positive voltage value given by the sum of the voltage drops across the sensing diodes 131 conducting the current. In other words, if the probe 140 contacts a sensing region 110, the same will be crossed by a current flowing in the opposite direction with respect to the current flowing through the protection diode 133. Therefore, if during the testing procedure it is possible to induce a current in both directions, it can be assumed that the probe 140 is short circuiting at least one sensing region 110 and the probe region 115.

Since the probe region 115 is connected to the ESD protection diode 133, the sensing structure 300, or more precisely the probe region 115, can also be advantageously used for connecting an integrated circuit in the substrate to the other external electrical systems and can therefore be used, for instance as a generic traditional pad during normal operation of the integrated circuit. At the same time, the probe region 115 may also be used as a detecting region in a similar manner as the sensing region 110.

Although the diodes 131 were used as sensing elements 130, the sensing elements 130 may be formed by other electronic components, such as, for instance, transistors or resistors and each sensing element 130 may include one more of these components.

Figure 12:
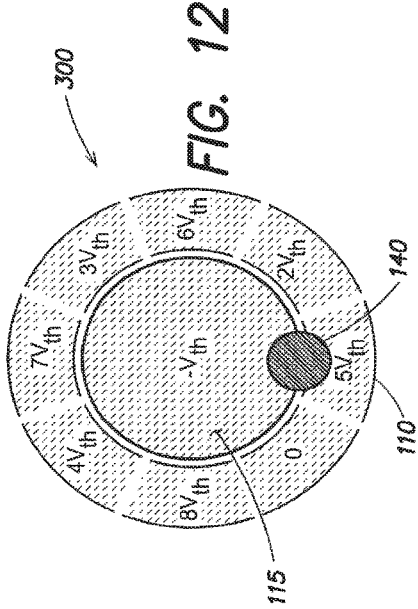
FIGS. 12 and 13 are schematic drawings illustrating the sensing arrangement of FIG. 11 during operation.
Figure 13:
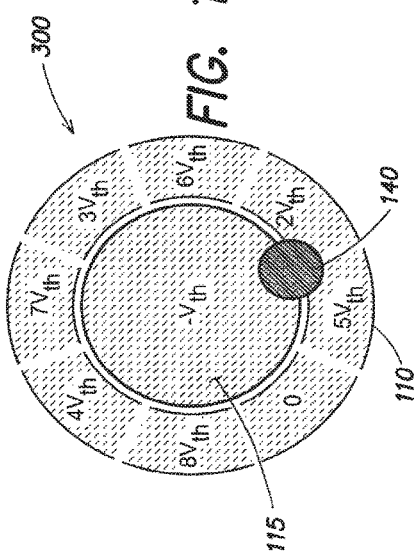

FIGS. 12 and 13 illustrate two examples of an operation of the sensing structure 300. More precisely, in the example of FIG. 12, the probe 140 contacts both the probe region 115 and the sensing region 110, which is connected to the ground electrode through 5 sensing diodes 131. In this case, the current can flow through the probe in two directions and the probe 140 will measure a potential of at least $-V_{th}$ if the current flows through the protection diode 133 or it will measure a value of at least $5 \cdot V_{th}$ if the current flows through the sensing circuit 130. As shown in FIG. 13, if the probe short circuits more than one sensing region 110 and the probe region 115, if current flows through the sensing circuit 130, the probe will assume the potential closer to the ground potential.

On the contrary, if the current can only flow in one direction, the probe 140 will be contacting only with the probe region 115 or only with the sensing regions 110.

Figure 15:
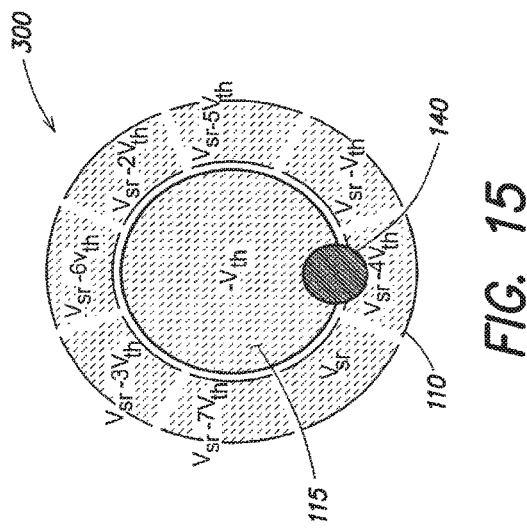
FIG. 15 is a schematic drawing illustrating the sensing arrangement of FIG. 14 during operation.
Figure 14:
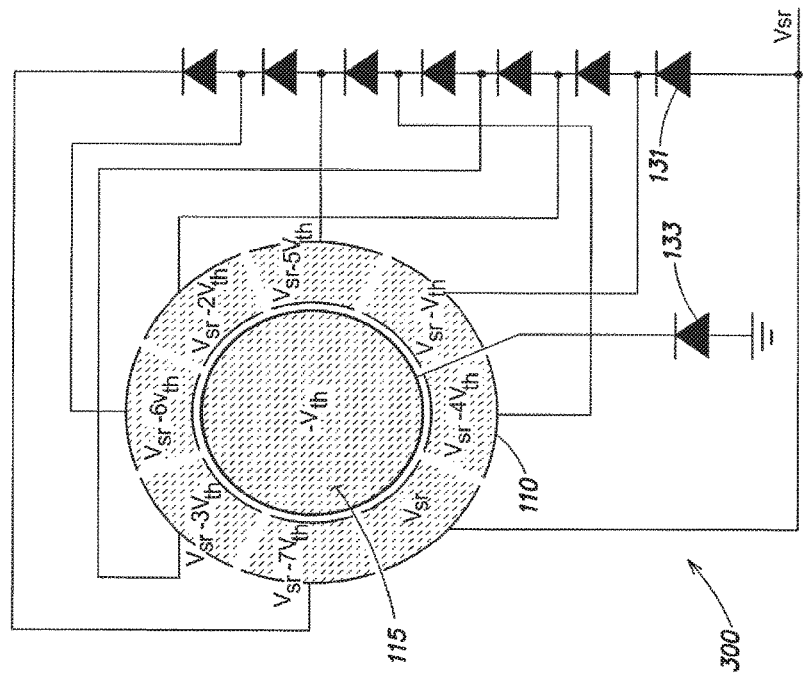
FIG. 14 is a schematic drawing illustrating a sensing arrangement.

In FIG. 11 the sensing circuit 130 and the protection diode 133 are both connected to a ground electrode. However, it is also possible to provide a sensing structure 300 wherein the sensing circuit 130 is connected to a reference potential $V_{sr}$ different from the ground potential, as shown in the example in FIGS. 14 and 15. In this example, if the probe 140 contacts a sensing region 110, it will measure a potential value referred to the reference voltage $V_{sr}$.

Figure 16:
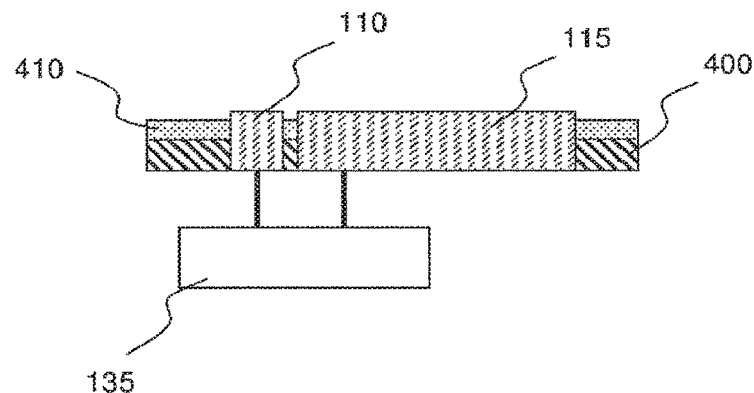
FIGS. 16 to 18 are sectional views of a sensing structure according to alternative realizations.
Figure 17:
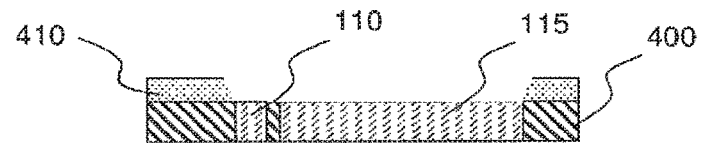
Figure 18:
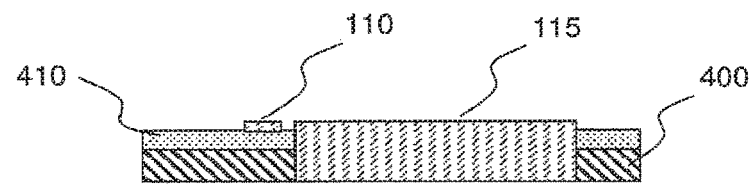

FIGS. 16 to 18 show a sectional view of a sensing structure 100, 200 and 300. In FIG. 16, the probe region 115 and the sensing regions 110 are integrated in a first non-conductive layer 400. Moreover, a passivation layer 410 lies on top of the first non-conductive layer 400 and surrounds the sensing regions 110 and the probe region 115. The sensing structure 100, 200, 300 may protrude from the passivation. Alternatively, as shown in FIG. 17, the sensing structure 100, 200, 300 is integrated in the first non-conductive layer 400 and is surrounded by a passivation layer 410. The sensing structure 300 may be arranged in the first non-conductive layer 400 such that the sensing regions 110 and the probe region 115 do not protrude from the first non-conductive layer. In this example, the passivation layer 410 surrounds the sensing structure 100, 200, 300 but does not lie between the sensing regions 110 and the probe region 115. The sensing regions 110 and a probe region 115 are isolated by means of the first non-conductive layer 400.

FIG. 18 shows an alternative realization of the sensing structure 100, 200, 300. Accordingly, the probe region 115 is in the first non-conductive layer 400, is surrounded by a passivation layer 410 and protrudes from the latter. In this example, the sensing regions 110 include conductive material, such as a metal arranged on the passivation layer 410. Since the sensing regions are only used in the testing phase for verifying alignment of the probe 140, they are not exposed to excessive mechanical stresses. Therefore, the sensing regions 110 are created using only one level of conductive material, such as a metal, and are connected to the sensing circuit 135 by means of a small pad 112 in the passivation layer 410 and by means of vias connections 420 (vertical interconnect accesses) and metal lines or metals 430. On the other hand, since the probe region 115 is exposed to high mechanical stresses during the testing phase and during assembly of the packaged device, it will be realized using several metallization levels or metals.

Figure 19:
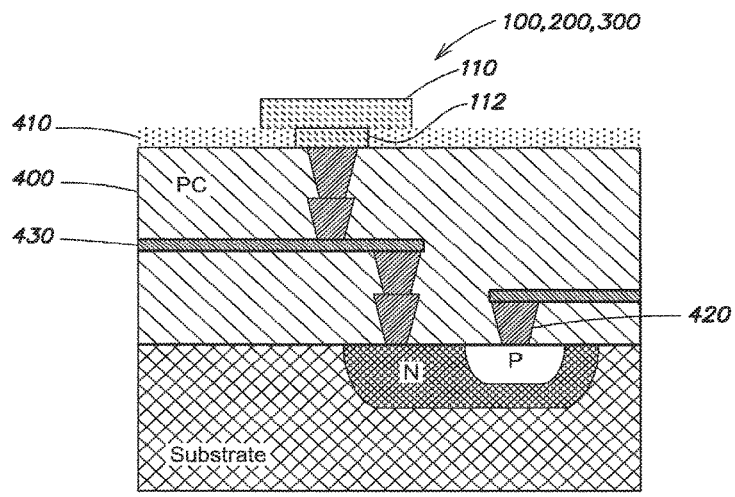
FIG. 19 shows a sectional view of a substrate comprising a sensing structure according to the realization of FIG. 18.

FIG. 19 shows a detailed sectional view of the connection between the sensing region 110 and the metals in the non-conductive substrate 400. Since in the examples of FIGS. 18 and 19 only the probe region 115 is realized using several layers of metal, it is possible to reduce the space/volume needed for realizing the sensing structure 100, 200, 300.

In the aforementioned sensing structures the sensing regions 110 and the probe region 115 may be pads which are finished in NiPd or NiPdAu.

The structure and the design of the sensing structure 100, 200, 300 can be optimized and simplified knowing the movement, slide or scrub direction of the probe 140 on the probe region 115 or on the pad. In particular, if the probe 140 moves on the substrate only in one direction, the sensing regions can be reduced to two. Alternatively, if the probe region 115 includes connection terminals or conductive pads connected to the integrated circuit, the sensing structure may be designed so as to include one sensing region 110 and one probe region 115.

Figures 20, 21, 22:
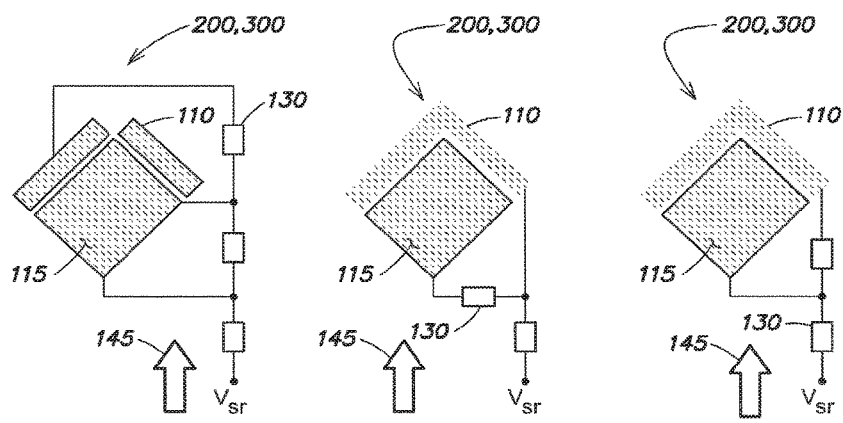
FIGS. 20 to 24 are schematic drawings illustrating further examples of the sensing structure.

FIGS. 20 to 22 illustrate several examples of a sensing structure 200, 300 optimized based on the scrub direction 145 of the probe 140. More precisely, FIG. 20 shows a sensing structure 200, 300 including a probe region 115 and two sensing regions 110. Advantageously, the probe region 115 is here rotated by 45 degrees with respect to common probe regions or pads that have generally a square or rectangular shape and aligned. Thus, the probe 140 will have a larger area on which it can slide, thereby allowing reducing the area of the probe region 115. The sensing regions 110 and the probe region 115 are connected to the corresponding sensing elements 130 as described above. Moreover, the probe region 115 is further connected to a reference potential through a further sensing element 130. If the reference potential is the ground voltage and the sensing elements 130 are sensing diodes 131, the probe region 115 can be used as an active region, as for instance a pad for connecting an integrated circuit with other systems. FIGS. 21 and 22 illustrate alternative design of a sensing structure 200, 300 including a probe region 115 and a sensing region 110. The sensing structure is advantageously simplified by including only one sensing region 110, thereby reducing the complexity of the structure and the space occupied by the complete sensing structure 100, 200. FIGS. 21 and 22 alternatively illustrate sensing structures 200, 300 including two sensing regions 110.

The sensing regions illustrated in FIGS. 20 to 22 can also be connected to two connection terminals or pads or electrodes.

Figure 23:
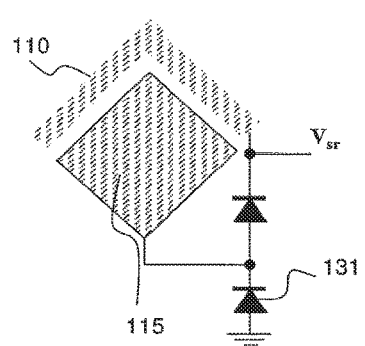
Figure 24:
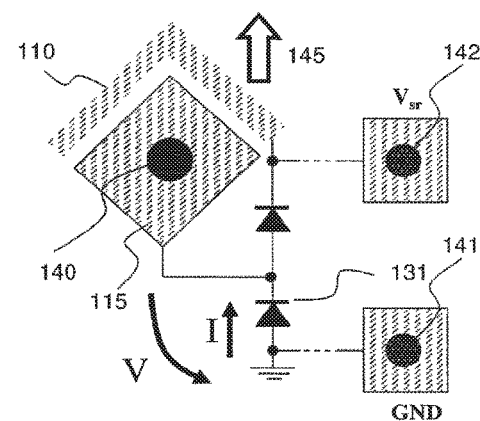

FIGS. 23 and 24 illustrate an example of such a sensing structure. Although the example describes a sensing structure 200, 300 including two sensing regions, or a sensing region 110 and a probe region 115, it may be possible to design sensing structures including any number of sensing regions. According to FIG. 23, the probe region 115 is connected to a ground electrode through a diode 131. This diode can be seen as a protecting element 133 and in this case the probe region 115 results in being connected to an ESD protection element. Further, the sensing region 110 is connected to a reference potential $V_{sr}$. If the reference potential is chosen as being a power supply voltage, the sensing structure may be also used as an active structure included in the ESD protection circuits.

During operation of the sensing structure 200, 300 the reference potential $V_{sr}$ and the ground potential may be provided by means of a ground probe 141 and a reference voltage probe 142 connected to respective ground and reference pads.

In order to determine the position of the probe 140 a current may be induced from the ground pad to the probe 140. If between the ground probe 141 and the probe 140 and between the probe 140 and the reference probe 142, the same voltage $V_{th}$ is measured, the probe 140 will be within the probe region 115. Otherwise, if between the ground probe 141 and the probe 140 is measured a voltage of at least $2 \cdot V_{th}$, while between the probe 140 and the reference probe 142 is measured a null voltage, the probe 140 will be on the sensing region 110. Finally, if between the ground probe 141 and the probe 140 is measured a voltage of $V_{th}$, while between the probe 140 and the reference probe 142 is measured a zero voltage, it can be derived that the probe 140 is in contact with both the probe region 115 and the sensing region 110. In this case, between the ground probe 141 and the reference probe 142 is measured a tension of $V_{th}$.

Although the sensing structure 200, 300 of FIGS. 23 and 24 is connected to the power supply voltage by means of a pad and to ground by means of another pad, during the testing phase the sensing structure 200, 300 may be connected to any reference potential different from the power supply and/or ground potential.

According to an embodiment, a sensing arrangement 450 including a plurality of sensing structures 100, 200, 300 is provided.

Figure 25:
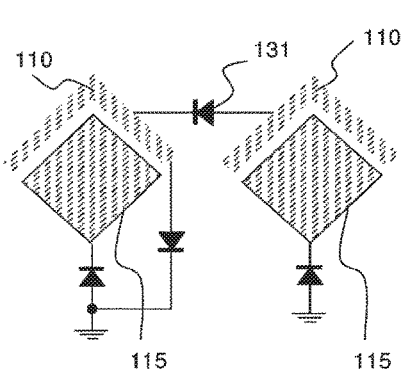
FIGS. 25 to 28 are schematic drawings illustrating possible arrangements of a plurality of sensing structures.

As illustrated in FIG. 25, the sensing arrangement 450 includes two sensing structures 100, 200, 300 connected to each other by means of a sensing element 130. In the particular example of FIG. 25, the sensing regions 110 of two sensing structures 100, 200, 300 are connected through a sensing diode 131.

Figure 26:
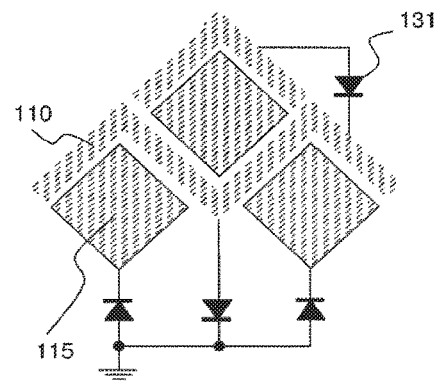

FIG. 26 shows a sensing arrangement 450 including a cluster of sensing structures 100, 200, 300. Said cluster may include several active regions and a sensing region 110 common to several sensing structures 100, 200, 300. Adjacent clusters may be further connected through a sensing diode 131.

Figure 27:
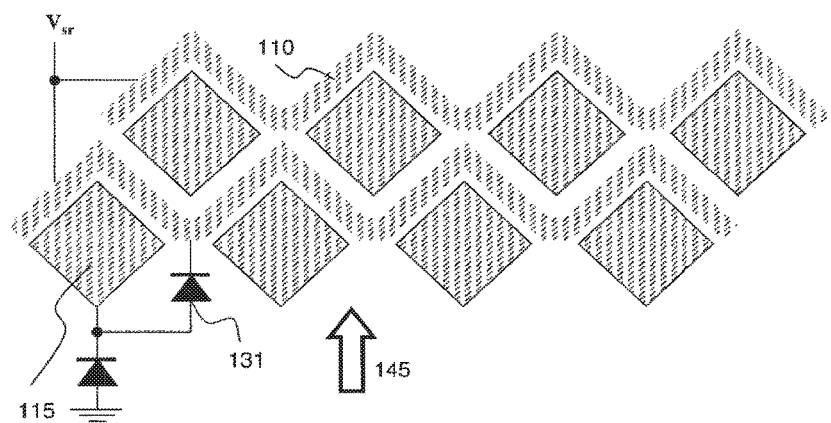

The sensing arrangement 450 may also include one or more rows of sensing structures 100, 200, 300, as illustrated in FIG. 27. According to this embodiment sensing structures 100, 200, 300 in the same row may have a common sensing region 110 which may be arranged based on the moving direction of an array of probes 140. Further, the sensing structures 100, 200, 300 may be connected to a reference potential and to a ground potential as described in the example of FIGS. 23 and 24. According to this arrangement, since all the sensing regions 110 are connected to each other, only one of the sensing regions 110, has to be connected to the ground terminal in order to have an array of active sensing structures 100, 200, 300.

Figure 28:
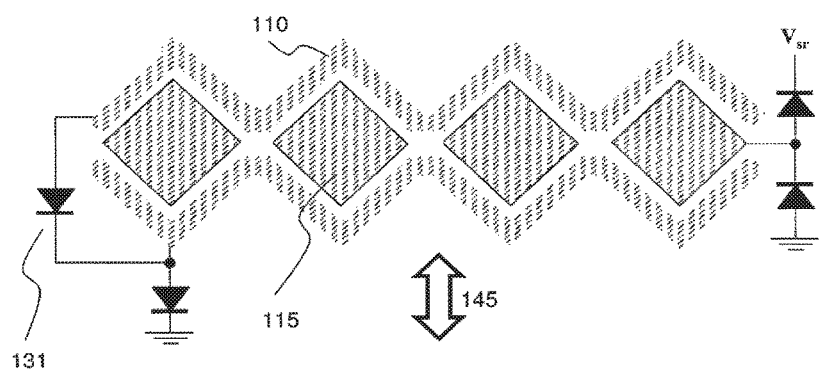

Although in the example of FIG. 27 only one sensing region is provided for each array of sensing structures 100, 200, 300, it is also possible to have arrays of sensing structures 100, 200, 300 including two or more sensing regions as shown in FIG. 28. This realization is particularly useful if the moving direction of the array of probes 140 is not known.

Figure 29:
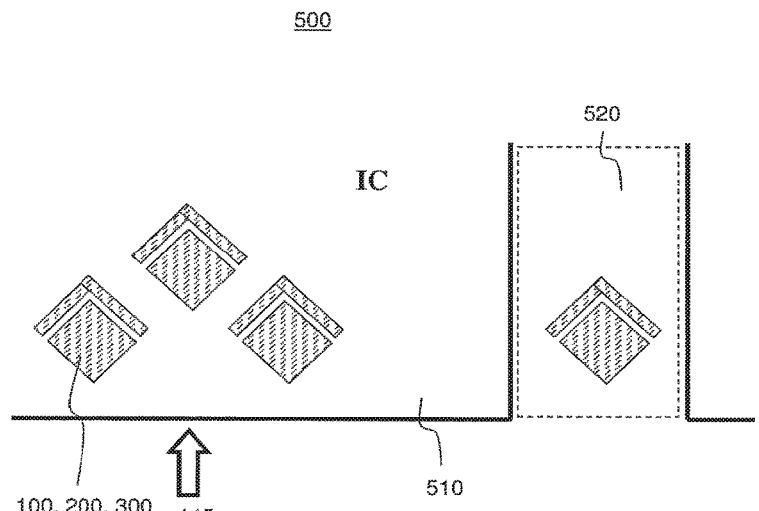
FIGS. 29 to 31 are schematic drawings illustrating substrates for integrated circuits.

A substrate 500 for integrated circuits may include the sensing regions 100, 200, 300 or the sensing arrangement 450. The substrate 500 may be, for instance, a wafer. As illustrated in FIG. 29 the sensing structures 100, 200, 300 may be located in the area 510 of the integrated circuit or may be located in a separation line or scribe line 520 located between adjacent device areas 510 on the substrate 500. Alternatively, the sensing structures 100, 200, 300 and the sensing arrangement 450 may be arranged on a dummy substrate that does not include any integrated circuits to be tested.

Advantageously, if the sensing structure 100, 200, 300 and the sensing arrangement 450 are located in the scribe line 520, said structures will not occupy space in the integrated circuit area 510 which may be entirely dedicated to said integrated circuit. Moreover, if the sensing structures in the scribe line include an active sensing structure 100, 200, 300, due to a connection terminal or pad, this can be used for testing elementary circuits or TEG (Test Element Group) located in the scribe line of the substrate.

Figure 30:
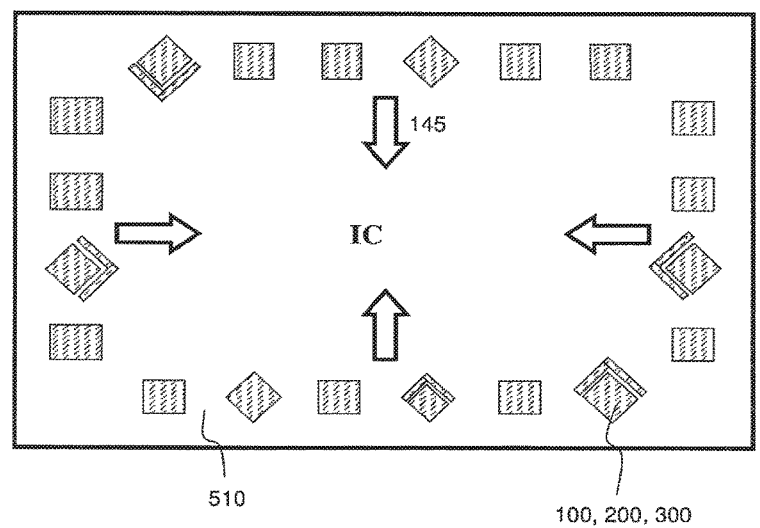
Figure 31:
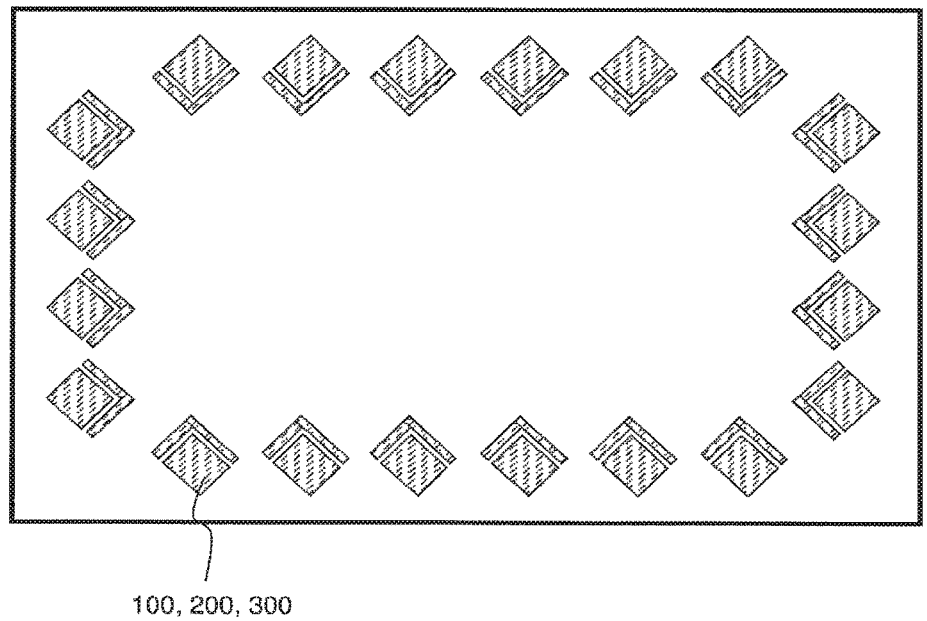

As shown in FIGS. 30 and 31, the sensing structures 100, 200, 300 and the sensing arrangement 450 may be located along the edges of the integrated circuit 510. Alternatively, the sensing structures may be located in correspondence of critical probes 140 of the array, such as peripheral probes or longer probes 140 of the array of probes of the probe card. Since the sensing structures 300 can also be used for connecting to integrated circuits, the integrated circuit 510 may be designed for including only sensing structure, which will be used for verifying alignment of the probes 140, for testing the integrated circuits of the substrate, and as connection terminals in the end product.

Figure 32:
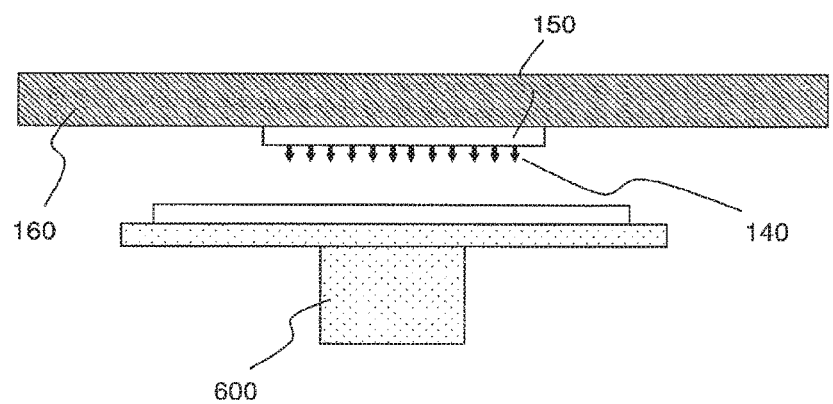
FIG. 32 is a schematic drawing illustrating a testing system.

Equipment for testing integrated circuits in the substrate 500 is partially shown in FIG. 32, and includes a probe array 150 including at least one probe 140. The probe array 150 may connect to probe card 160 including a printed circuit board, and the substrate 500 including at least one sensing structure 100, 200, 300. The substrate 500 may be arranged onto a support 600 chuck and included into a device prober which is not shown here.

Figure 33:
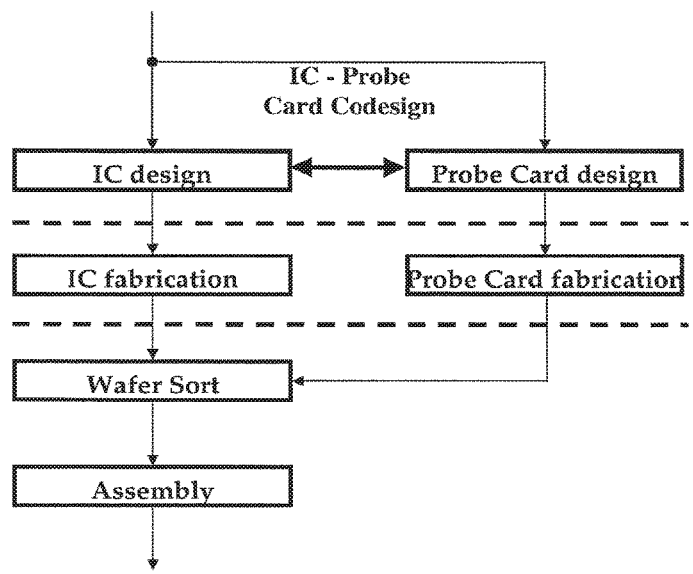
FIG. 33 is a detailed block diagram illustrating design steps for realizing a substrate for integrated circuits and a probe card for testing the substrate.
Figures 34, 35:
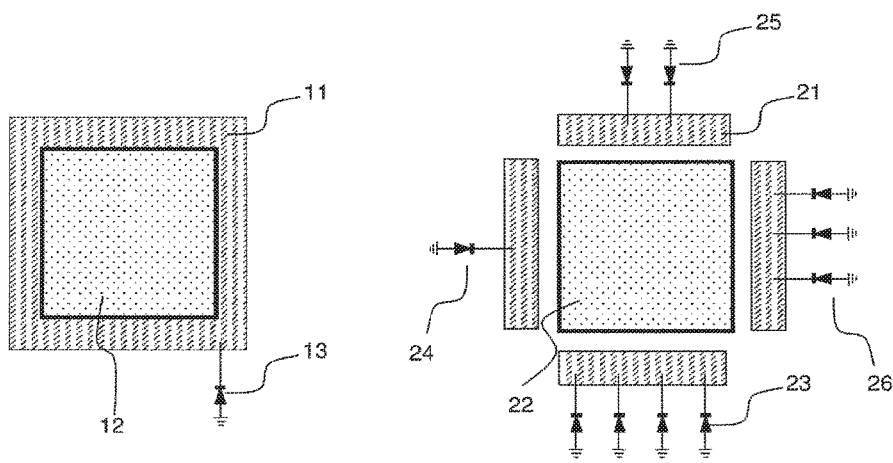
FIGS. 34 and 35 are schematic drawings illustrating sensing structures according to the prior art.
Figure 36:
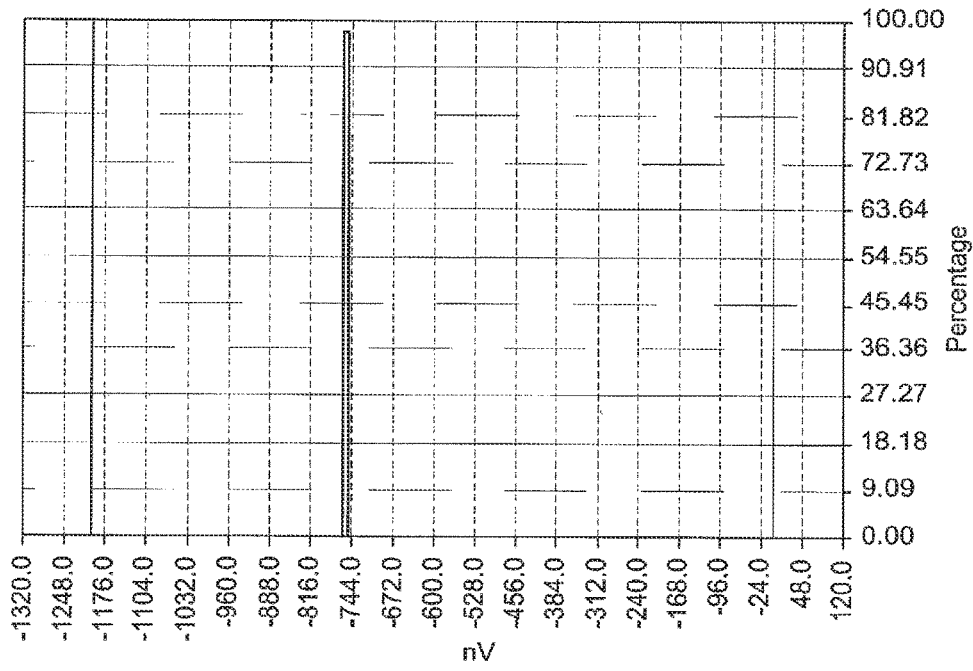
FIG. 36 is a histogram showing the results of several measurements of a sensing structure in optimal conditions.
Figure 37:
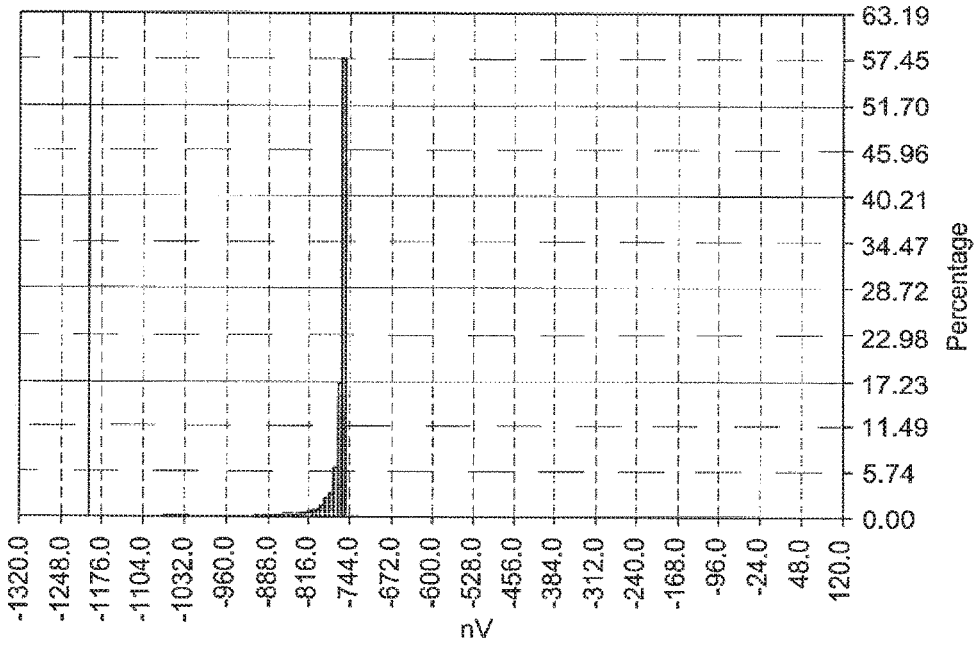
FIG. 37 is a histogram showing the results of measurements performed on a sensing pad in non-optimal conditions.

The optimal design of the position of the sensing structures 100, 200, 300 on the integrated circuit 510 essentially depends on the design of the circuit elements forming said integrated circuit 510 and on the scrub direction of the various probes 140. Therefore, in order to reduce the number of sensing regions needed for verifying the position of the probes 140, it may be advantageous to jointly design the integrated circuit 510 and the probe card 160. This process is schematically illustrated in the flow diagram of FIG. 33. More precisely, the probe card 160 to be used in the testing phase will be designed based on the design of the integrated circuits 510 on the substrate 500. Subsequently, the probe card 160 so produced may be used for performing the electrical test on the EWS on the substrate 500 and finally, the integrated circuit device can be assembled.

If the sensing structures 100, 200, 300 are placed in the scribe line 520, the joint design of the probe card and lithographic masks has to be performed by placing the sensing structures 100, 200, 300 in the array of integrated circuits that said mask will realize.

Therefore, the embodiments relate to improved sensing structures 100, 200, 300 capable of unambiguously determining a drift direction of a probe 140 with respect to the sensing structure 100, 200, 300 without being affected by variations in the measured values due to non-optimal electrical contacts between the sensing structure 100, 200, 300 and a probe 140.

In the embodiments, the electrical connection between the sensing structure 100, 200, 300 and the probe 140 is obtained by contacting the probe 140 with the sensing regions 110 and 115. However, in a further not illustrated embodiment, the probe 140 may be electrically connected to the sensing structure 100, 200, 300 by other means that do not necessarily require a direct electrical contact between probe 140 and sensing structure 100, 200, 300. As an example, in the case that the sensing structure and the probe can operate at radiofrequencies, the tip of the probe 140 may be for instance used as a capacitive interface conducting a variable current. Consequently, the sensing elements 130 may also include responsive elements such as inductances or capacitors or transmission lines. In any case, such a structure may be useful if the probe 140 operates at radiofrequencies.

Of course, in order to satisfy contingent and specific requirements, a skilled person may apply several modifications to the previously described solutions. Although the present invention has been described with reference to preferred embodiments, it should be clear that various omissions, replacements and modifications in the design and details, such as other embodiments are possible; it is further clearly intended that specific elements and/or method steps described in relation with any embodiment of the described invention ca be incorporated in any other embodiment in conjunction with the state of the art as general aspects of design choices.

The invention claimed is:

1. A sensing structure for use in testing an integrated circuit on a substrate, the sensing structure comprising:
    a layer of non-conductive material having a top surface;
    a conductive probe region surrounded by the layer of non-conductive material and having a top surface that is co-planar with the top surface of the layer of non-conductive material;
    a first conductive sensing element region surrounded by the layer of non-conductive material and having a top surface that is co-planar with the top surface of the layer of non-conductive material;
wherein the first conductive sensing element region is electrically insulated from the conductive probe region by the layer of non-conductive material;
a layer of passivation material in contact with the top surface of the layer of non-conductive material and having a single opening extending therethrough which exposes the top surfaces of the conductive probe region and the first conductive sensing element region; and
a first diode having a first terminal electrically connected to the conductive probe region and a second terminal electrically connected to the first conductive sensing element region.

2. The sensing structure of claim 1, wherein the first terminal of the first diode is a cathode terminal and the second terminal of the first diode is an anode terminal.

3. The sensing structure of claim 1, further comprising a second diode having a first terminal electrically connected to the conductive probe region and a second terminal electrically connected to a reference voltage node.

4. The sensing structure of claim 3, wherein the first terminal of the first diode is an anode terminal, the second terminal of the first diode is a cathode terminal, the first terminal of the second diode is a cathode terminal and the second terminal of the second diode is an anode terminal.

5. The sensing structure of claim 1, wherein the first conductive sensing element region at least partially surrounds the conductive probe region.

6. The sensing structure of claim 5, wherein the conductive probe region has a circular shape in plan view and the first conductive sensing element region has an arcuate shape in plan view.

7. The sensing structure of claim 5, wherein the conductive probe region has a square shape in plan view and the first conductive sensing element region includes linear segments extending along side edges of the square shape.

8. A sensing structure for use in testing an integrated circuit on a substrate, the sensing structure comprising:
a layer of non-conductive material having a top surface;
a conductive probe region surrounded by the layer of non-conductive material and having a top surface that is co-planar with the top surface of the layer of non-conductive material;
a first conductive sensing element region surrounded by the layer of non-conductive material and having a top surface that is co-planar with the top surface of the layer of non-conductive material;
wherein the first conductive sensing element region is electrically insulated from the conductive probe region by the layer of non-conductive material;
a second conductive sensing element region surrounded by the layer of non-conductive material and having a top surface that is co-planar with the top surface of the layer of non-conductive material and the top surface of the first conductive sensing element region;
wherein the second conductive sensing element region is electrically insulated from the conductive probe region and the first conductive sensing element region by the layer of non-conductive material; and
a layer of passivation material in contact with the top surface of the layer of non-conductive material and having a single opening extending through the layer of passivation material which exposes the top surfaces of the conductive probe region and the first and second conductive sensing element regions.

9. The sensing structure of claim 8, further comprising a first diode having a first terminal electrically connected to the first conductive sensing element region and a second terminal electrically connected to the second conductive sensing element region.

10. The sensing structure of claim 9, wherein the first terminal of the first diode is a cathode terminal and the second terminal of the first diode is an anode terminal.

11. The sensing structure of claim 9, further comprising a second diode having a first terminal electrically connected to the first conductive sensing element region and a second terminal electrically connected to a reference voltage node.

12. The sensing structure of claim 11, wherein the first terminal of the first diode is an anode terminal, the second terminal of the first diode is a cathode terminal, the first terminal of the second diode is an anode terminal and the second terminal of the second diode is a cathode terminal.

13. The sensing structure of claim 11, further comprising a third diode having a first terminal electrically connected to the conductive probe region and a second terminal electrically connected to a reference voltage node.

14. The sensing structure of claim 13, wherein the first terminal of the first diode is an anode terminal, the second terminal of the first diode is a cathode terminal, the first terminal of the second diode is an anode terminal, the second terminal of the second diode is a cathode terminal, the first terminal of the third diode is a cathode terminal and the second terminal of the third diode is an anode terminal.

15. The sensing structure of claim 11, further comprising a third diode having a first terminal electrically connected to the conductive probe region and a second terminal electrically connected to a ground node.

16. The sensing structure of claim 15, wherein the first terminal of the first diode is an anode terminal, the second terminal of the first diode is a cathode terminal, the first terminal of the second diode is an anode terminal, the second terminal of the second diode is a cathode terminal, the first terminal of the third diode is a cathode terminal and the second terminal of the third diode is an anode terminal.

17. The sensing structure of claim 8, wherein the first and second conductive sensing element regions at least partially surround the conductive probe region.

18. The sensing structure of claim 17, wherein the conductive probe region has a circular shape in plan view and each of the first and second conductive sensing element regions has an arcuate shape in plan view.

19. The sensing structure of claim 17, wherein the conductive probe region has a square shape in plan view and each of the first and second conductive sensing element regions include linear segments extending along side edges of the square shape.

20. The sensing structure of claim 8, wherein the first conductive sensing element region at least partially surrounds the conductive probe region.

21. The sensing structure of claim 20, wherein the conductive probe region has a circular shape in plan view and the first conductive sensing element region has an arcuate shape in plan view.

22. The sensing structure of claim 20, wherein the conductive probe region has a square shape in plan view and the first conductive sensing element region includes linear segments extending along side edges of the square shape.

* * * * *